(12) United States Patent
Stephenson

(10) Patent No.: US 6,959,609 B2
(45) Date of Patent: Nov. 1, 2005

(54) INFERENTIAL DENSOMETER AND MASS FLOWMETER

(75) Inventor: Stanley V. Stephenson, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 19 days.

(21) Appl. No.: 10/670,411

(22) Filed: Sep. 24, 2003

(65) Prior Publication Data

US 2005/0061061 A1 Mar. 24, 2005

(51) Int. Cl.⁷ .............................. G01F 1/74; G01F 7/00
(52) U.S. Cl. ...................................... 73/861.04; 73/197
(58) Field of Search ............................ 73/861.04, 195, 73/196, 197

(56) References Cited

U.S. PATENT DOCUMENTS

| | | | |
|---|---|---|---|
| 4,604,902 A | * | 8/1986 | Sabin et al. .............. 73/861.04 |
| 5,461,930 A | | 10/1995 | Farchi et al. ............. 73/861.04 |
| 5,535,632 A | | 7/1996 | Kolpak ..................... 73/861.04 |
| 5,654,502 A | | 8/1997 | Dutton ..................... 73/152.18 |
| 6,327,914 B1 | | 12/2001 | Dutton .................... 73/861.356 |

* cited by examiner

*Primary Examiner*—Harshad Patel
(74) *Attorney, Agent, or Firm*—John W. Wustenberg; Baker Botts L.L.P.

(57) ABSTRACT

A system for measuring the density and mass flow rate of a fluid stream. The system generally comprises a volumetric flow device, a momentum device, and a data processing device. The present invention also provides methods for using such system.

20 Claims, 3 Drawing Sheets

INFERENTIAL DENSOMETER AND MASS FLOWMETER

BACKGROUND

The present invention relates generally to systems and methods for measuring parameters of a fluid stream. More particularly, the invention relates to an inferential densometer and mass flowmeter.

Certain exemplary embodiments of existing densometers utilize radioactive elements to measure the density of fluids. The use of such radioactive densometers may be problematic because of the need for additional procedures and precautions to ensure the densometer is handled safely. The use of existing non-radioactive densometers, such as Coriolis meters, is also problematic. For example, the largest embodiments of such meters typically have a flow area of no larger than about 3 inches in diameter; however, most subterranean treatment operations employ fluid piping having about a 4 inch to about an 8 inch diameter. Thus, conventional non-radioactive densometers, even in their largest embodiments, cannot accommodate the flow of the entire stream for most subterranean treatment operations. Accordingly, the majority of the flow is typically piped around such non-radioactive densometers, through a 1 inch or 2 inch diameter bypass pipe, while only a small portion of the flow is actually measured through the densometer. Accordingly, one cannot be certain that such a non-radioactive densometer is measuring a representative portion of the flow stream.

Pressure limitations also pose a problem for conventional non-radioactive densometers. Such densometers typically are limited to a maximum fluid pressure of between 150 psi to about 300 psi. However, numerous subterranean treatment operations are conducted at operating pressures of up to about 15,000 psi, which often necessitates the use of densometers that have been proven to withstand "proof" pressures of up to about 22,500 psi. Accordingly, conventional non-radioactive densometers are suitable only for low pressure applications.

SUMMARY

The present invention relates generally to flow measurement devices; more particularly, the invention relates to an inferential densometer and mass flowmeter.

In one embodiment, the present invention is directed to a method for determining at least one parameter of a fluid stream, comprising the steps of: measuring the volumetric flow rate of the fluid stream; measuring the momentum rate of the fluid stream; and calculating the at least one parameter using the volumetric flow rate and the momentum rate of the fluid stream. The at least one parameter may be selected from the group consisting of density and mass flow rate.

In another embodiment, the present invention is directed to a system for determining at least one parameter of a fluid stream, the fluid stream having a volumetric flow rate and a momentum rate, comprising: a volumetric flow device for measuring the volumetric flow rate of a fluid stream; a momentum device for measuring the momentum rate of a fluid stream, connected in fluid communication in series with the volumetric flow device; and a data processing device electronically connected to the volumetric flow device and the momentum device for determining the at least one parameter. The at least one parameter may be selected from the group consisting of density and mass flow rate.

The features and advantages of the present invention will be readily apparent to those skilled in the art upon a reading of the description of the exemplary embodiments, which follows.

BRIEF DESCRIPTION OF THE DRAWINGS

A more complete understanding of the present disclosure and advantages thereof may be acquired by referring to the following description taken in conjunction with the accompanying figures, wherein.

Figure 1:
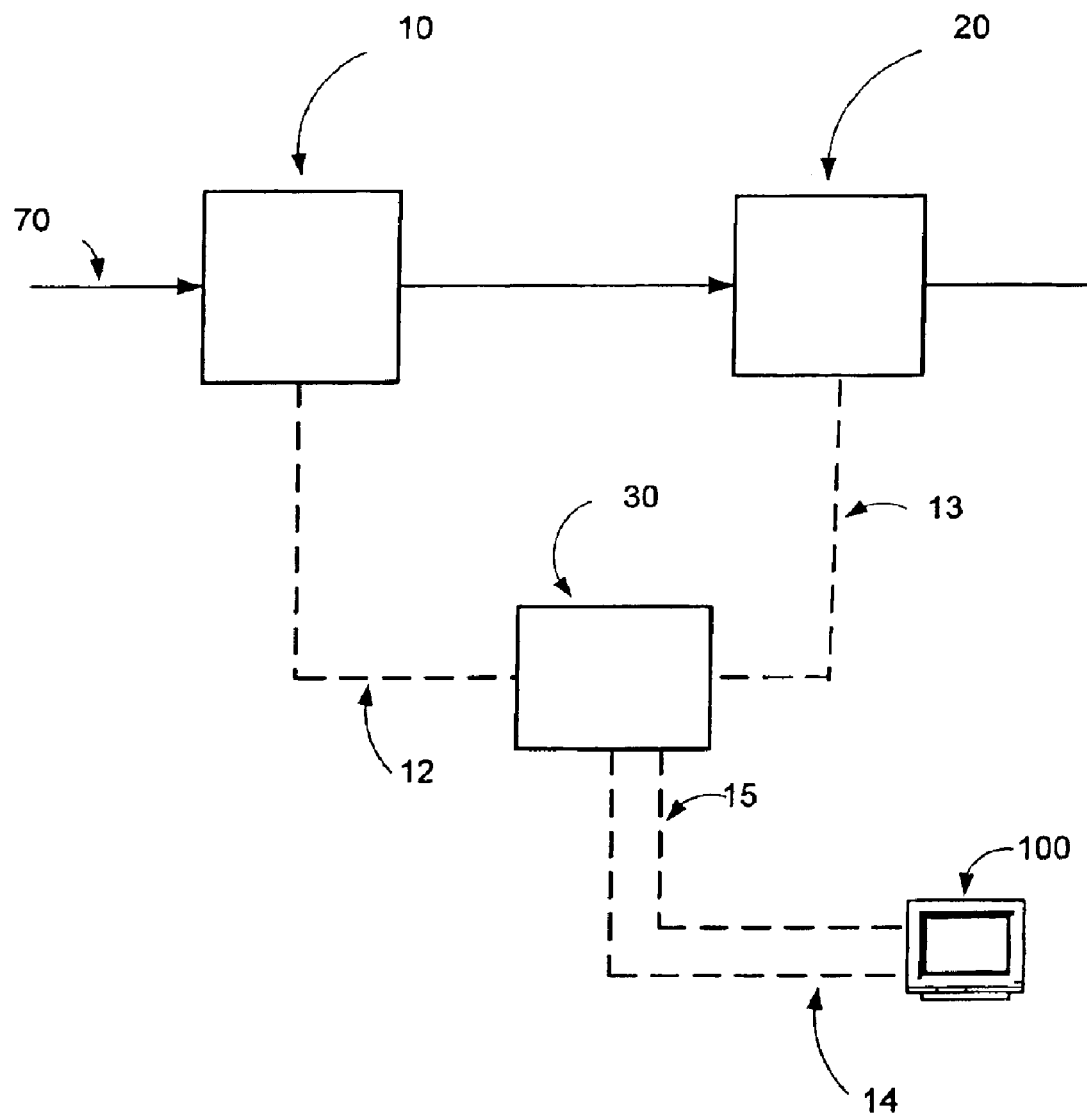
FIG. 1 illustrates a schematic diagram of an inferential densometer in accordance with the present invention.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF EXEMPLARY EMBODIMENTS

In one exemplary embodiment, the present invention is directed to a system, which system comprises a volumetric flow device, a momentum device, and a data processing device. One exemplary embodiment of the system is capable of accepting the entirety of a given flow stream at operating pressures up to about 15,000 psi. The system is further capable of accepting multi-phase flow streams, wherein the flow stream may comprise multiple liquid phases, or at least one liquid phase having solid matter entrained or suspended therein. Where a flow stream comprises two or more liquids, the system of the present invention will provide a bulk density measurement, e.g., a density measurement for the overall stream.

Referring now to FIG. 1, a volumetric flow device is shown at 10. Preferably, volumetric flow device 10 is placed directly in the flow path of fluid stream 70, whose density and mass flow rate are being measured. Volumetric flow device 10 may comprise any device that measures a volumetric flow rate of fluid stream 70 and transmits such flow rate to data processing device 30 as output signal 12. Examples of a suitable volumetric flow device 10 include but are not limited to turbine flow meters, magnetic flow meters or positive displacement metering pumps or flow meters. In certain exemplary embodiments where volumetric flow device 10 is a positive displacement metering pump, a sensor and transmitter must be affixed to the pump so as to measure the pump speed and subsequently transmit such speed as output signal 12 to data processing device 30. Certain exemplary embodiments of a suitable volumetric flow device 10 may be constructed so as to have a fluid flow area having an internal diameter of up to about 8 inches. Additionally, certain exemplary embodiments of a suitable volumetric flow device 10 can be capable of withstanding "proof" pressures of up to about 22,500 psi.

Output signal 12 can be a current, a voltage or a frequency, among other forms, depending on factors such as the nature of volumetric flow device 10. For example, if a turbine flow meter is used as volumetric flow device 10, output signal 12 can be a frequency; if a magnetic flow meter is used as volumetric flow device 10, output signal 12 can be a current or a frequency. The use of a current as output signal 12 is thought to be more favorable than the use of a voltage, as a current may be less susceptible to changes in resistance in the signal path.

Volumetric flow device 10 is in fluid connection with a momentum device 20. More specifically, in one exemplary embodiment, momentum device 20 is connected in series with volumetric flow device 10, as shown in FIG. 1. Momentum device 20 can comprise any device which measures a momentum rate of fluid stream 70 and transmits that momentum rate to data processing device 30 as output signal 13. Examples of a suitable momentum device 20 include but are not limited to wedge meters, venturis, orifice meters and the like. Certain exemplary embodiments of such a momentum device 20 can be constructed so as to have a fluid flow area having an internal diameter of up to about 8 inches. Further, certain exemplary embodiments of such a momentum device 20 can be capable of withstanding proof pressures of up to about 22,500 psi. When selecting a particular momentum device 20, a relevant factor may be the fact that an orifice meter may suffer from abrasion from prolonged operation, whereas the wedge element of a wedge meter can be made from materials with sufficient hardness to endure prolonged operation. In certain exemplary embodiments, the momentum device 20 is a wedge meter.

Output signal 13 can be a current or a voltage, depending on factors such as the nature of momentum device 20. For example, if a wedge meter is used as momentum device 20, output signal 13 can be a current or voltage. The use of a current as output signal 13 is thought to be more favorable than the use of a voltage, as a current may be less susceptible to changes in resistance in the signal path.

In the exemplary embodiment shown in FIG. 1, data processing device 30 receives output signals 12 and 13, determines the mass flow rate and density of fluid stream 70, and transmits such mass flow rate as output signal 14 and such density as output signal 15. Generally, data processing device 30 is any device capable of receiving a plurality of signals, manipulating such signals to determine a mass flow rate and a density, and generating output signals representing such mass flow rate and density. In certain exemplary embodiments, data processing device 30 comprises a pre-processing system which produces an output as either a current or a frequency, proportional to the density. An example of a suitable data processing device 30 is a computer having the capability of accepting multiple input signals and generating multiple output signals. Output signals 14 and 15 may be a current, or a frequency, or any other output known to one of ordinary skill in the art. Output signals 14 and 15 may further be displayed on monitor 100 or transmitted to another computer for use therein in calculations incorporating mass flow rate or density.

Data processing device 30 solves the following two equations to determine a mass flow rate and density of the fluid:

Density "$\rho$"=$(K^*C)/Q^2$;  Equation 1

Mass flow rate "$M$"=$Q^*\rho$;  Equation 2 where

Q=volumetric flow rate from output signal 12;

K=lumped dimensional and units correction constant; and

C=momentum rate from output signal 13.

For example, in an exemplary embodiment where fluid stream 70 passes first through volumetric flow device 10 and subsequently through momentum device 20, volumetric flow device 10 will measure the volumetric flow rate Q, which it will then transmit as output signal 12 to data processing device 30. Momentum device 20 will measure the momentum rate C of fluid stream 70, which it will then transmit as output signal 13 to data processing device 30. The lumped dimensional and units correction constant K is a correction constant for the entire system, and comprises a volumetric flow meter coefficient (known for any volumetric flow device 10) and a units conversion constant which facilitates providing a mass flow rate and/or density measurement having the desired units. Accordingly, in an exemplary embodiment, data processing device 30 can solve Equation 1 to determine the density of fluid stream 70, and solve Equation 2 to determine the mass flow rate of fluid stream 70. Such determinations are made internally within data processing device 30 using methods recognizable by those skilled in the art with the benefit of this disclosure.

The volumetric flow device 10 and momentum device 20 of the present invention can be installed anywhere in a fluid flow line, including surface and subterranean installations. Where components of the system are located downhole, they may be placed downhole via a wireline, which may also serve as a power source. Alternatively, the components may be placed downhole by assembling such devices on a drill string, typically on the inside. In certain of these embodiments, mud pulse telemetry may be used. Typically, where mud pulse telemetry is used, the components of the system must be battery powered for the length of time they are to remain downhole. One of ordinary skill in the art, with the benefit of this disclosure, will recognize how the systems and methods of the present invention may be used in connection with mud pulse telemetry. In certain exemplary embodiments, the components of the system are installed at the surface.

Figure 2:
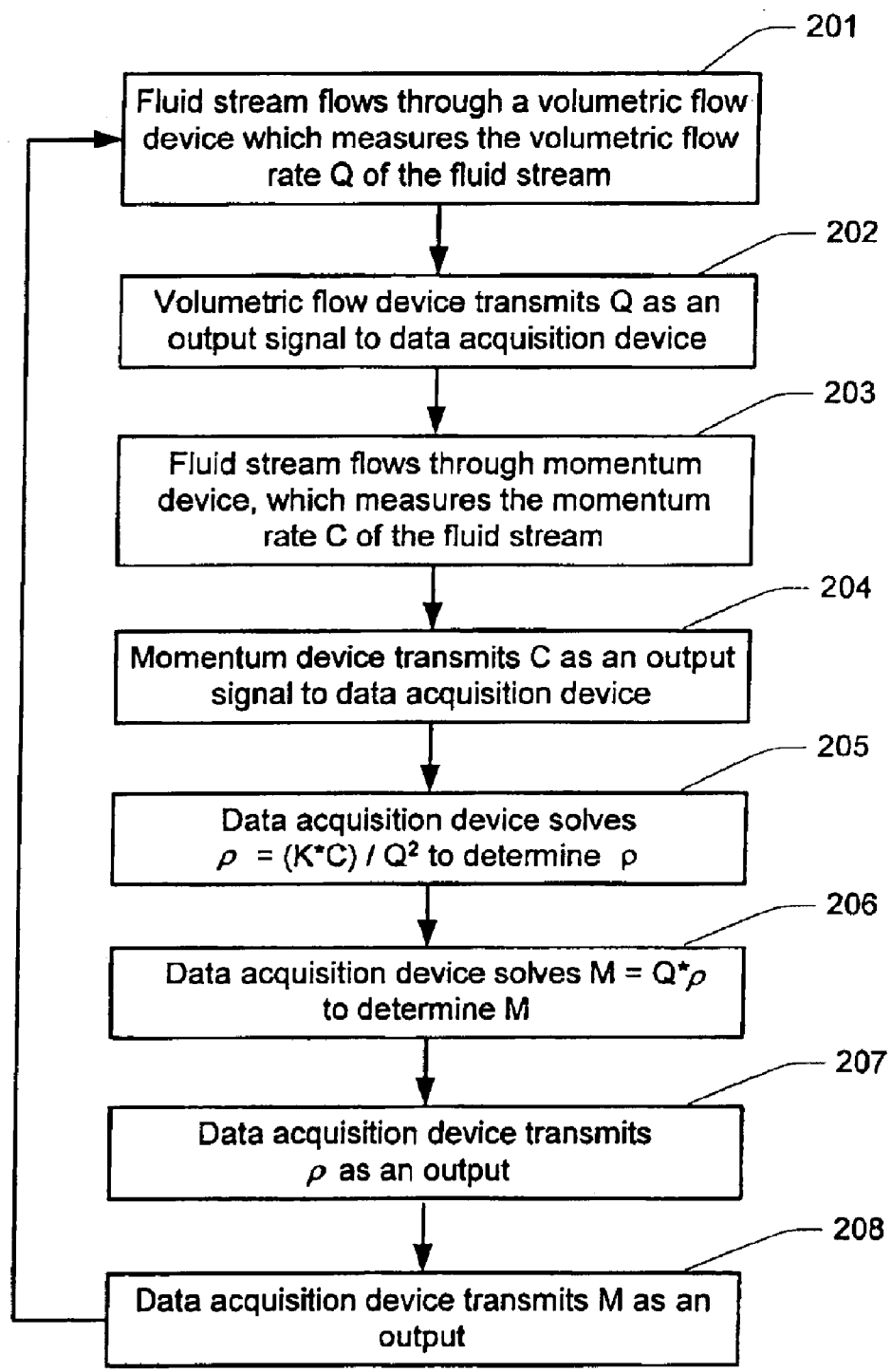
FIG. 2 illustrates a process flow diagram for an exemplary method of the present invention.

An exemplary embodiment of a method of the present invention is illustrated in FIG. 2. In step 201, fluid stream 70 flows through volumetric flow device 10, which measures the volumetric flow rate Q of the fluid stream 70. In step 202, the volumetric flow device 10 transmits the measured volumetric flow rate Q as output signal 12 to data processing device 30. In step 203, the fluid stream 70 flows through momentum device 20, which measures the momentum rate C of the fluid stream 70. In step 204, the momentum device 20 transmits the measured momentum rate C as output signal 13 to the data processing device 30. In step 205, the data processing device 30 solves the equation: $\rho=(K^*C)/Q^2$ to determine the density $\rho$. In step 206, the data processing device 30 solves the equation: $M=Q^*\rho$ to determine the mass flow rate M. In step 207, the data processing device 30 transmits the density $\rho$ as output signal 15, which output signal 15 can, for example, appear on monitor 100, or can be received by another device for use in calculations involving the density $\rho$. In step 208, the data processing device 30 transmits the mass flow rate M as output signal 14, which output signal 14 can, for example, appear on monitor 100, or can be received by another device for use in calculations involving the mass flow rate M. The process then returns to step 201. As those of ordinary skill in the art will recognize, step 208 can precede step 207, and step 207 can precede step 206.

Figure 3:
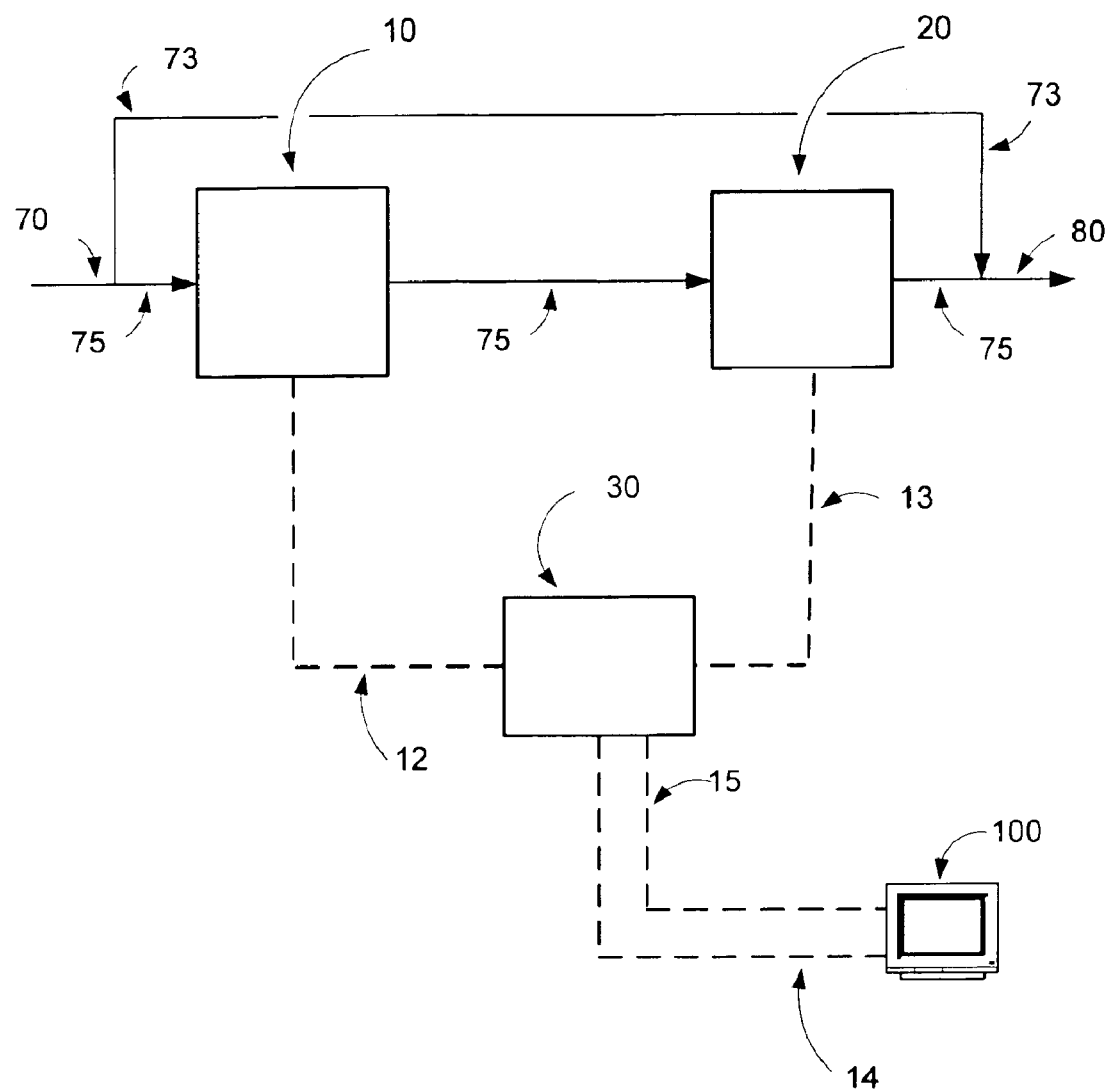
FIG. 3 illustrates a schematic diagram of an inferential densometer in accordance with the oresent invention.

FIG. 3 illustrates a schematic diagram of another embodiment of an inferential densometer in accordance with the present invention. As illustrated therein, fluid stream 70 may be separated into two portions, first portion 73 and second portion 75. Second portion 75 may flow through volumetric flow device 10 and momentum device 20, while first portion 73 may bypass volumetric flow device 10 and momentum device 20. First portion 73 and second portion 75 then may be recombined to form fluid stream 80, as illustrated in FIG. 3.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A method of determining at least one parameter of a fluid stream for subterranean treatment operations, comprising the steps of:

measuring the volumetric flow rate of the fluid stream;

measuring the momentum rate of the fluid stream; and calculating the at least one parameter using the volumetric flow rate and the momentum rate of the fluid stream;

wherein:
   the fluid stream does not comprise gas phase; and
   the fluid stream comprises phases selected from the group consisting of:
   at least one liquid phase; and
   a solid phase and at least one liquid phase.

2. The method of claim 1 wherein the fluid stream has a mass flow rate and a density, and the at least one parameter is selected from the group consisting of the mass flow rate of the fluid stream and the density of the fluid stream.

3. The method of claim 2 further comprising the step of transmitting the momentum rate of the fluid stream to a data processing device.

4. The method of claim 3 further comprising the step of transmitting the volumetric flow rate of the fluid stream to a data processing device.

5. The method of claim 4 wherein:

the at least one parameter is the mass flow rate of the fluid stream;

the density of the fluid stream is known; and the step of calculating the at least one parameter further comprises the step of using the data processing device to determine the mass flow rate of the fluid stream by multiplying the volumetric flow rate of the fluid stream by the density of the fluid stream.

6. The method of claim 4 wherein:

the at least one parameter is the density of the fluid stream; and the step of calculating the at least one parameter further comprises the step of using the data processing device to determine the density of the fluid stream by multiplying the momentum rate of the fluid stream by a numerical constant, and then dividing the product by the square of the volumetric flow rate of the fluid stream.

7. The method of claim 4 wherein the step of calculating the at least one parameter comprises the steps of:

using the data processing device to determine the density of the fluid stream by multiplying the momentum rate of the fluid stream by a numerical constant, and then dividing the product by the square of the volumetric flow rate of the fluid stream; and using the data processing device to determine the mass flow rate of the fluid stream by multiplying the volumetric flow rate of the fluid stream by the density of the fluid stream.

8. The method of claim 1 wherein the step of measuring the volumetric flow rate of the fluid stream comprises the step of flowing a portion of the fluid stream through a volumetric flow device.

9. The method of claim 1 wherein the step of measuring the volumetric flow rate of the fluid stream comprises the step of flowing the entirety of the fluid stream through a volumetric flow device.

10. The method of claim 1 wherein the step of measuring the momentum rate of the fluid stream comprises the step of flowing a portion of the fluid stream through a momentum device.

11. The method of claim 1 wherein the step of measuring the momentum rate of the fluid stream comprises the step of flowing the entirety of the fluid stream through a momentum device.

12. A system for determining at least one parameter of a fluid stream for subterranean treatment operations, the fluid stream having a volumetric flow rate and a momentum rate, comprising:

a volumetric flow device for measuring the volumetric flow rate of the fluid stream;

a momentum device for measuring the momentum rate of the fluid stream; and a data processing device connected to the volumetric flow device and the momentum device for determining the at least one parameter;

wherein:
   the fluid stream does not comprise a gas phase; and
   the fluid stream comprises phases selected from the group consisting of:
   at least one liquid phase; and
   a solid phase and at least one liquid phase.

13. The system of claim 12 wherein the at least one parameter is selected from the group consisting of mass flow rate and density.

14. The system of claim 12 wherein the volumetric flow device comprises a turbine flow meter, a magnetic flow meter, or a positive displacement metering pump having a speed sensor and transmitter.

15. The system of claim 12 wherein the momentum device comprises a wedge meter, an orifice, or a venturi.

16. The system of claim 12 wherein the data processing device comprises a computer capable of receiving multiple inputs and producing at least one output.

17. The system of claim 16 wherein the data processing device receives as input an output signal from the volumetric flow device and an output signal from the momentum device, and produces at least one output.

18. The system of claim 12 wherein:

the at least one parameter is the mass flow rate of the fluid stream;

the density of the fluid stream is known; and the data processing device determines the at least one parameter by multiplying the density of the fluid stream by the volumetric flow rate of the fluid stream.

19. The system of claim 12 wherein:

the at least one parameter is the density of the fluid stream; and the data processing device determines the at least one parameter by multiplying the momentum rate of the fluid stream by a numerical constant, and then dividing the product by the square of the volumetric flow rate of the fluid stream.

20. The system of claim 12 wherein the momentum device is connected in fluid communication in series with the volumetric flow device.

* * * * *